United States Patent [19]
Davis et al.

[11] Patent Number: 5,217,438
[45] Date of Patent: Jun. 8, 1993

[54] NEEDLE STOP AND SAFETY SHEATH

[75] Inventors: Richard E. Davis, Grand Rapids; Warren D. Lun, Battle Creek, both of Mich.

[73] Assignee: DLP, Inc., Grand Rapids, Mich.

[21] Appl. No.: 916,597

[22] Filed: Jul. 20, 1992

[51] Int. Cl.⁵ .............................................. A61M 5/32
[52] U.S. Cl. .................................. 604/198; 604/117; 403/229
[58] Field of Search ............... 128/749; 604/117, 192, 604/198; 403/229

[56] References Cited
U.S. PATENT DOCUMENTS

| | | |
|---|---|---|
| 1,085,505 | 1/1914 | Stafford ............................ 403/229 |
| 1,436,707 | 11/1922 | Gaschke . |
| 2,852,797 | 9/1958 | Daubenspeck ..................... 403/229 |
| 3,230,595 | 1/1966 | Kedem . |
| 3,477,437 | 11/1969 | Goldberg . |
| 4,022,191 | 5/1977 | Jamshidi . |
| 4,508,419 | 4/1985 | Galindo ............................. 604/117 |
| 5,067,946 | 11/1991 | Zhadanov ......................... 604/198 |

*Primary Examiner*—Max Hindenburg

[57] ABSTRACT

A needle stop for a biopsy needle or the like in the form of a spring having coils in firm engagement with the surface of the shaft of the needle. Ends of the spring may be pinched to enlarge the coils and permit movement of the stop along the shaft. A guard tube is associated with the stop for covering the point of the needle when not in use.

8 Claims, 3 Drawing Sheets

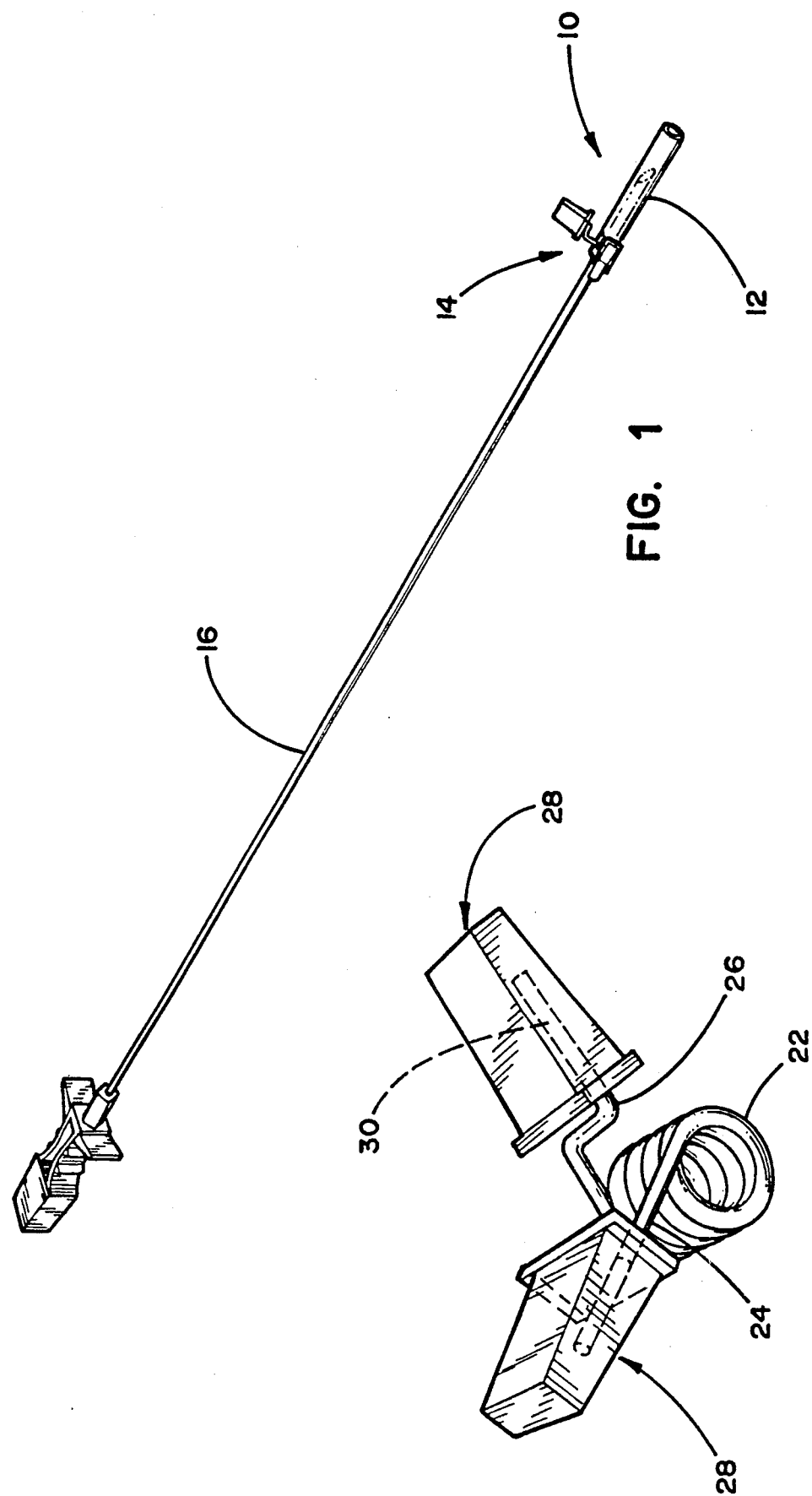

NEEDLE STOP AND SAFETY SHEATH

BACKGROUND OF THE INVENTION

1. Field of the Invention

The present invention relates to depth gauges for biopsy needles or other medical needles and in one embodiment of the invention, to such a needle depth gauge incorporating a tip guard adapted to cover the sharp point of the needle when it is not in use.

2. Description of Related Art

Needles are commonly employed to obtain biopsy specimens for laboratory evaluation. This entails a surgical procedure which requires that the surgeon know precisely the depth to which the needle is inserted in the patient's tissue to be sure that a proper specimen is obtained. Typically, spaced markings are provided along the surface of the needle to indicate the depth of penetration of its tip. A depth stop may be employed to limit penetration of the needle to the desired depth.

U.S. Pat. No. 3,477,437, issued Nov. 11, 1969 to A. M. Goldberg, discloses a depth stop comprising an open-wound metal coil spring which grips the smooth outer surface of a hypodermic needle to be used in performing a thoracentesis procedure. The surgeon first inserts the needle to the proper depth, then places the coil spring on the needle shaft by wedging the latter between adjacent coils of spring, so that the spring extends laterally from the needle to form a stop which will ensure that the needle will not inadvertently be inserted to a greater depth during the procedure. The Goldberg coil spring may be adjusted along the length of the needle shaft after it is first wedged in place, but such adjustment is awkward because the spring is not easily unsprung to decrease the friction between needle and spring.

U.S. Pat. No. 1,436,707, issued Nov. 28, 1922 to G. Gaschke, also discloses a stop guard for hypodermic needles, which in this instance comprises a length of spring steel bent into a V-shape and formed with a pair of aligned perforations through which the needle shaft is passed. Tension on the needle shaft from the spring metal holds the guard in place. When adjustment is required, the user may squeeze the ends of the spring steel together, thus releasing the frictional hold on the needle shaft, and then slide the stop along the needle shaft to the appropriate position. Because the spring metal engages the needle in a limited contact area, a large spring force is required to provide a frictional force great enough to hold the stop from sliding. The high spring force, on the other hand, makes unspringing the device difficult. It is also to be noted that the Gaschke stop guard does not provide any protection against the needle's sharp point when the needle is not in use.

U.S. Pat. No. 4,022,191, issued May 10, 1977 to K. Jamshidi, discloses a coaxial biopsy needle guard and depth stop. More particularly, a tubular sleeve guard is attached to the hub of a syringe and fits over the needle, so that the entire needle is enclosed within the sleeve guard. The guard is formed with a series of circumferential grooves spaced along its length so that a preselected longitudinal portion of the guard may be broken off. The portion remaining provides a depth stop to limit travel of the needle into the body. The Jamshidi guard permits only a limited number of preset depths, and is nonfunctional as a needle guard once a portion is broken off to form a depth stop.

U.S. Pat. No. 5,067,946, issued Nov. 26, 1991 to S. Zhadanov, discloses a needle guard formed as an inner tube which fits over and holds the shaft of a needle, and an outer tube adjustable along the shaft of the needle by means of a pinionlike finger wheel having teeth which engage racklike teeth on the inner tube. When pressure on the wheel is released, it locks in the rotational position in which it is disposed at the time, and the interengaged teeth thereby prevent movement of the outer tube relative to the needle shaft. The outer tube thus comprises an adjustable protective tube having a limited range of motion, which may be easily moved to cover or uncover the needle's sharp point. The design is relatively complex, requiring two coaxial tubes to cover the needle, and a toothed wheel carried by the outer tube. Further, the protective cover may be adjusted over only a small distance because the wheel cooperates with a limited number of teeth formed on the first tube. It is also pointed out that nothing in the disclosure of the Zhadanov patent implies that the device might function as a depth stop.

SUMMARY OF THE INVENTION

In accordance with the present invention, a needle depth gauge has been designed which performs a dual function. The first is to provide a depth gauge suitable for quick one-handed operation which provides a relatively high clamping force for sure placement along the shaft of the biopsy needle. The second function is to provide a safety cover for the needle's sharp point or tip when the needle is not in use.

More particularly, the invention provides a stop for a biopsy needle or the like, which comprises a continuous wire spring formed in a series of adjacent coils thereof. The internal diameter of each of the coils in the unstressed condition is selected to be less than the outer diameter of the shaft of a preselected needle. The spring terminates in end portions thereof which extend outwardly from respective coils, the end portions being movable toward each other from the unstressed condition in a direction to expand the coils radially. When this is done, the needle shaft may be received in the coils and the stop moved longitudinally along the shaft. To releasably fix the stop longitudinally relative to the shaft the end portions of the spring are simply permitted to move apart and cause the coils to grip the surface of the needle shaft.

These and other features, objects and advantages of the invention will be apparent from the ensuing description in conjunction with the accompanying drawings and the appended claims.

THE DRAWINGS

In the drawings:

FIG. 1 is a perspective view of a biopsy needle showing the needle guard and depth stop of the invention carried on the needle at the distal or tip end thereof;

FIG. 4 is an enlarged perspective view of the spring locking mechanism of FIG. 3;

DESCRIPTION OF THE PREFERRED EMBODIMENT

Figure 3:
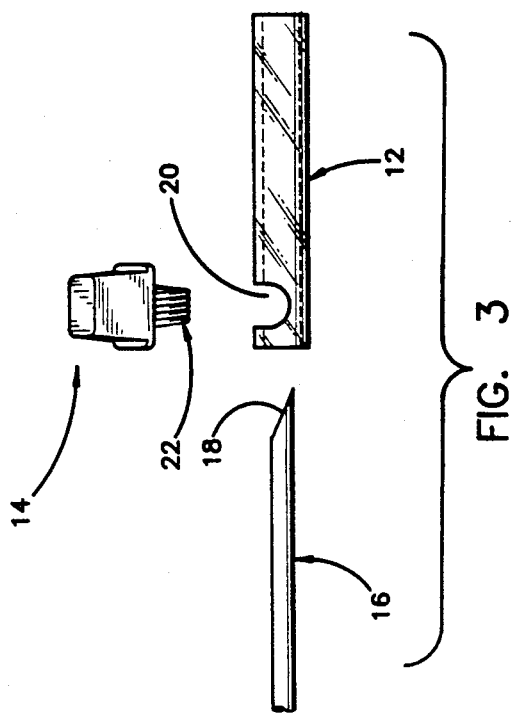
FIG. 3 is an exploded view of the needle guard and depth stop of FIG. 2, showing a spring locking mechanism and a guard tube thereof separated from the needle tip.
Figure 2:
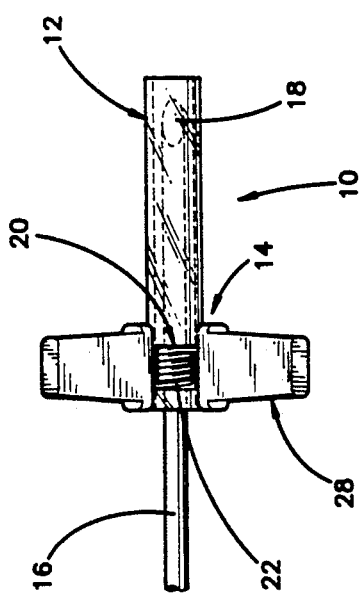
FIG. 2 is an enlarged plan view of the tip end of the needle with the needle guard and depth stop of FIG. 1.

Referring now to the drawings and to FIGS. 1, 2 and 3 in particular, the needle guard and depth gauge 10 in accordance with the invention comprises an open-ended guard tube 12 and a spring locking mechanism 14. It is intended for use with a biopsy needle 16 or other medical needle and is adapted to enclose the needle's sharp point 18 to prevent injury to the physician or others.

The inside diameter of guard tube 12, which comprises and open-ended sheath, is selected so that it will fit closely over needle 16 yet will slide freely along the needle. The wall of guard tube 12 is interrupted by a notch-shaped opening 20 which communicates with the interior thereof and is of a size to accept spring locking mechanism 14, as described with particularity hereinbelow. The tube may be made of any suitable material, but preferably of a polymer which is tough enough to protect needle point 18 and may be easily sterilized. The material is preferably transparent or translucent so that the position of needle point 18 within guard tube 12 can be visually verified.

As perhaps best seen in FIG. 4, spring locking mechanism 14 comprises a continuous wire spring formed in a series of adjacent spring coils 22, a first spring arm 24 extending tangentially outwardly from one of coils 22, a second spring arm 26 extending tangentially outwardly from an opposite one of the spring coils. Preferably included are a pair of handles 28 mounted respectively on the distal ends of arms 24 and 26.

When the spring locking mechanism is free of the needle, coils 22 are formed with a slightly smaller internal diameter in the unsprung or unstressed condition than the external diameter of needle 16 so that when spring locking mechanism 14 is in place on the needle, the latter will be firmly gripped by coils 22. By including a number of coils 22 in spring locking mechanism 14, a comparably large surface area is provided for grasping the needle 16 in a fast or firm grip without employing excessive spring force.

As noted hereinabove, arms 22 and 24 extend tangentially outwardly from coils 22. One 24 of the arms is straight, as shown in FIG. 4 for example, and the other arm 26 is bent into approximately a Z-form so that the distal ends of the arms project from coils 22 at approximately the same longitudinal location relative thereto.

Handles 28 on the distal ends of arms 24 and 26 may be of any configuration suitable for gripping by the user without difficulty or undue discomfort, especially between the thumb and forefinger. Handles 28 may be affixed in any suitable manner, but preferably, as shown in FIG. 4, by receiving the distal ends of arms 24 and 26 in elongate sockets 30 formed in handles 28, which in this instance are otherwise solid, and securing the connection by means of adhesive. Alternatively, handles 28 may be hollow and the distal end of each of arms 24 and 26 may be formed with a bend (not shown) in a manner to engage interior surfaces of handles 28 by spring force.

Figure 6:
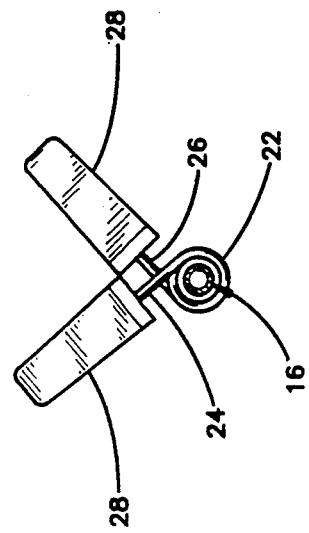
FIG. 6 is an end view similar to FIG. 5, but showing the spring locking mechanism in its sprung condition.
Figure 5:
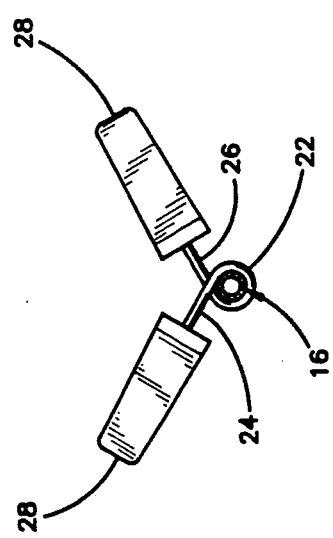
FIG. 5 is an end view of the spring locking mechanism of FIG. 3 in its unsprung condition and carried on the needle.

As shown in FIGS. 5 and 6, when spring arms 24 and 26 are pinched toward each other, coils 22 are sprung; that is, they are unwound or expanded slightly in the radial direction from the unsprung condition of FIG. 5, thereby releasing the friction hold they otherwise exert about the circumference of needle 16, as represented in FIG. 6, and allowing spring locking mechanism 14 to be moved freely along the length of the needle. Then, when spring arms 24 and 26 are released to permit them to return to the unsprung condition of FIG. 5, the spring coils again grip the needle shaft to remain releasably fixed at a particular longitudinal position relative to the needle.

Guard tube 12 may optionally be added to spring locking mechanism 14. Notch 20 of the tube is formed large enough for coils 22 of spring locking mechanism 14 to be received into the interior of the tube by way of the notch, with arms 24 and 26 remaining outside of the tube. Spring locking mechanism 14 and guard tube 12 thus become a unit to be applied to the needle, coils 22 being coaxial with the tube, and spring locking mechanism 14 may thus be employed to prevent or facilitate movement of guard tube 12 relative to needle 16 along its length.

Figure 7:
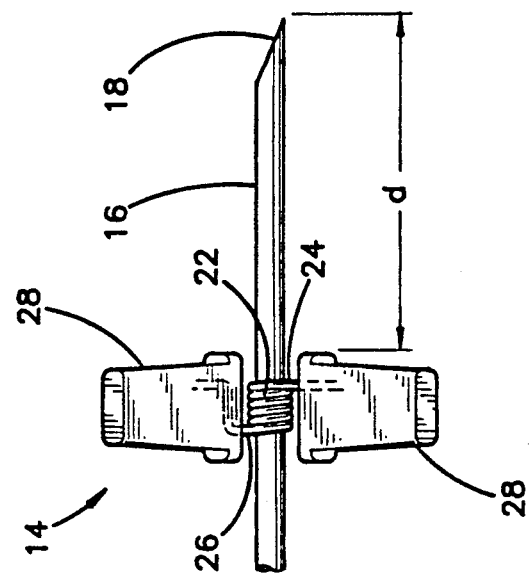
FIG. 7 is a plan view showing the spring locking mechanism of FIG. 3 in use as a depth gauge on the needle.

As shown in FIG. 7, the principal use of the invention is as a depth stop. When the physician wishes to remove a biopsy sample from a patient, he may spring or expand spring coils 22 by pinching handles 28 toward each other, then manually slide spring locking mechanism 14 away from the point of the needle to a predetermined or preselected distance therefrom, and finally release handles 28 to reset spring coils 22 in their unsprung condition to fix the spring locking mechanism at the predetermined or preselected distance from the point of the needle. When needle 16 is inserted into the body of a patient, engagement of the spring with the patient's body indicates that needle point 18 has penetrated to the proper depth.

Figure 8:
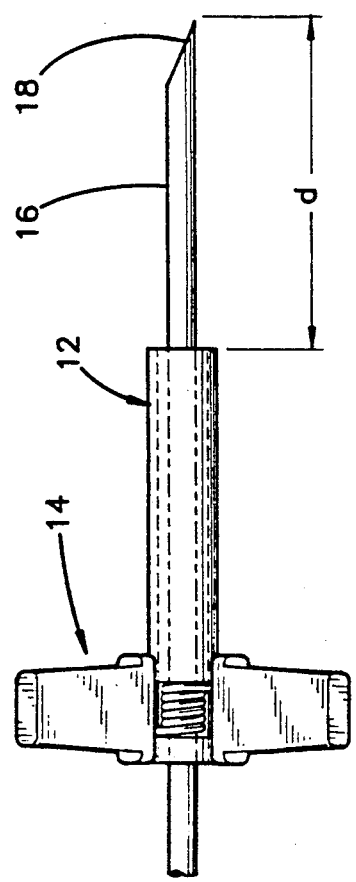
FIG. 8. is a view similar to FIG. 7 but showing the spring locking mechanism in use as a depth gauge in conjunction with the guard tube.

As shown in FIG. 8, the device of the invention may also be used as a needle stop with the guard tube 12 in place; depth d will be measured in this case to the distal end of guard tube 12. Whether the spring locking mechanism 14 is used alone or in conjunction with the guard tube 12, spaced markings (not shown) may be provided along the surface of the needle 16 to assist the user in measuring the depth d.

When needle 16 is not in use, guard tube 12 may be positioned so that the point or tip 18 of needle 16 is covered, as shown in FIGS. 1 and 2.

The device according to the invention provides the advantages of quick, one-handed operation, and relatively high clamping forces for sure placement along the shaft of a biopsy needle or the like. Ease of operation makes the device safe to use, with little possibility that a user will inadvertently injure himself with the needle. In addition, the tip of the needle may be covered when not in use.

While the invention has been described in connection with a specific embodiment thereof, it will be understood that this is by way of illustration and not of limitation, and that the scope of the appended claims should be construed as broadly as the prior art will permit.

What is claimed is:

1. A needle stop for a biopsy needle or the like, comprising a continuous wire spring formed in a series of adjacent coils thereof, the internal diameter of each of the coils in the unstressed condition being smaller than the outer diameter of a shaft of a preselected medical needle, the spring terminating in end portions thereof extending outwardly from respective ones of the coils, the end portions being movable toward each other in response to finger pressure from the unstressed condition in a direction to expand the coils radially so that the internal diameter of each of the coils is greater than the outer diameter of the shaft of the medical needle, whereby the needle shaft may be received in the coils and the stop moved longitudinally along the shaft, and whereby the stop may be releasably fixed longitudinally relative to the shaft by relieving finger pressure to permit the end portions to move apart and cause the coils to grip the surface of the needle shaft.

2. A needle stop according to claim 1, including a guard tube comprising an open-ended sheath movable with the spring and coaxial with the coils thereof.

3. A needle stop according to claim 2, wherein the guard tube is formed with a notch communicating with the interior thereof, the coils being received in the interior of the tube by way of the notch, the end portions of the spring extending outwardly of the tube at the notch.

4. A needle stop according to claim 1, including a pair of handles, each of the end portions of the spring carrying one of the handles thereon for manual engagement by a user of the stop.

5. A needle stop in combination with a medical needle, the needle stop comprising a continuous wire spring formed in a series of adjacent coils thereof, the internal diameter of each of the coils in the unstressed condition being less than the outer diameter of a shaft of a preselected needle, the spring terminating in end portions thereof extending outwardly from respective ones of the coils, the end portions being movable toward each other from the unstressed condition in a direction to expand the coils radially, whereby the needle shaft may be received in the coils and the stop moved longitudinally along the shaft, and whereby the stop may be releasably fixed longitudinally relative to the shaft by permitting the end portions to move apart and cause the coils to grip the surface of the needle shaft.

6. A needle stop in combination with a medical needle according to claim 5, including a pair of handles, each of the end portions of the spring carrying one of the handles thereon for manual engagement by a user of the stop.

7. A needle stop for a medical needle comprising a continuous wire spring formed in a series of adjacent coils thereof, the internal diameter of each of the coils in the unstressed condition being less than the outer diameter of a shaft of a preselected needle, the spring terminating in end portions thereof extending outwardly from respective ones of the coils, and a guard tube comprising an open-ended sheath movable with the spring and coaxial with the coils thereof, the end portions being movable toward each other from the unstressed condition in a direction to expand the coils radially, whereby the needle shaft may be received in the coils and the stop moved longitudinally along the shaft, and whereby the stop may be releasably fixed longitudinally relative to the shaft by permitting the end portions to move apart and cause the coils to grip the surface of the needle shaft.

8. A needle stop according to claim 7, wherein the guard tube is formed with a notch communicating with the interior thereof, the coils being received in the interior of the tube by way of the notch, the end portions of the spring extending outwardly of the tube at the notch.

* * * * *